United States Patent [19]

Portnoy

[11] Patent Number: 4,867,741
[45] Date of Patent: Sep. 19, 1989

[54] PHYSIOLOGICAL DRAINING SYSTEM WITH DIFFERENTIAL PRESSURE AND COMPENSATING VALVES

[76] Inventor: Harold D. Portnoy, 1431 Woodward Ave., Bloomfield Hills, Mich. 48013

[21] Appl. No.: 549,267

[22] Filed: Nov. 4, 1983

[51] Int. Cl.⁴ .............................................. A61M 5/00
[52] U.S. Cl. ..................................... 604/10; 137/510; 604/185
[58] Field of Search ....................... 604/8–10, 604/247, 185; 137/510

[56] References Cited

U.S. PATENT DOCUMENTS

| | | | |
|---|---|---|---|
| 3,111,125 | 11/1963 | Schulte | 604/9 |
| 3,503,402 | 3/1970 | Schulte | 604/9 |
| 3,756,243 | 9/1973 | Schulte | 604/9 |
| 3,768,508 | 10/1973 | Schulte | 604/9 |
| 3,769,982 | 11/1973 | Schulte | 604/9 |
| 3,901,245 | 8/1975 | Spitz et al. | 604/10 |
| 3,991,768 | 11/1976 | Portnoy | 604/10 |
| 3,999,553 | 12/1976 | Spitz et al. | 604/10 |
| 4,493,339 | 1/1985 | Porter, Jr. | 137/510 |

*Primary Examiner*—C. Fred Rosenbaum
*Assistant Examiner*—Mario Costantino
*Attorney, Agent, or Firm*—Donald D. Mon

[57] ABSTRACT

A compensating valve and a drainage system for draining a body fluid from one body region to another body region. The system enables routine drainage at predetermined differential pressures, provides for pumping action, for flushing action to clear the system of obstructive material, and for resisting over-drainage which can occur when the patient makes an abrupt and relatively large change in his position. A compensating valve purpose has a valving action which is proportional to various parameters so as to enable continuous and proportional control for drainage rather than an on/off control.

17 Claims, 3 Drawing Sheets

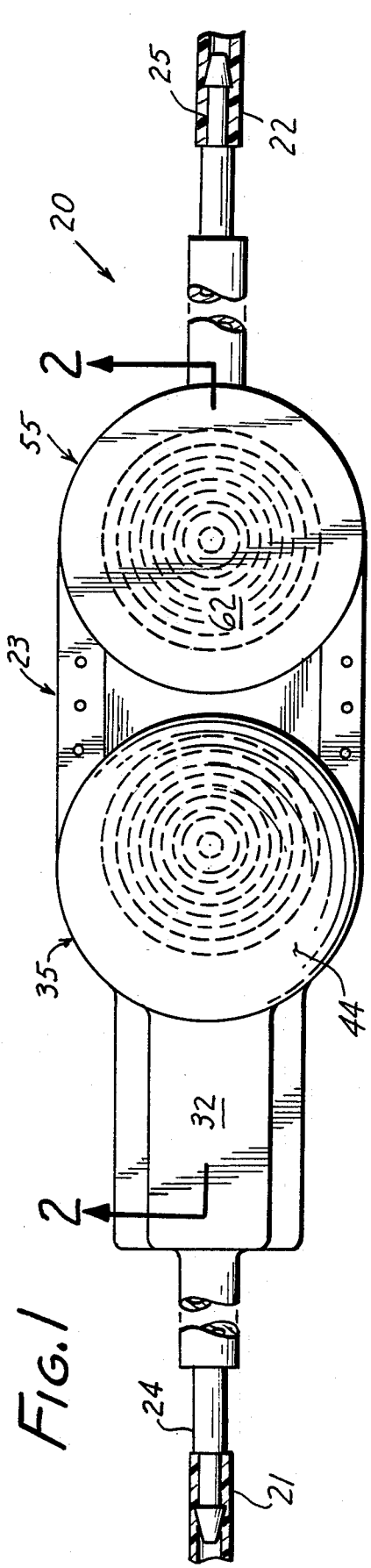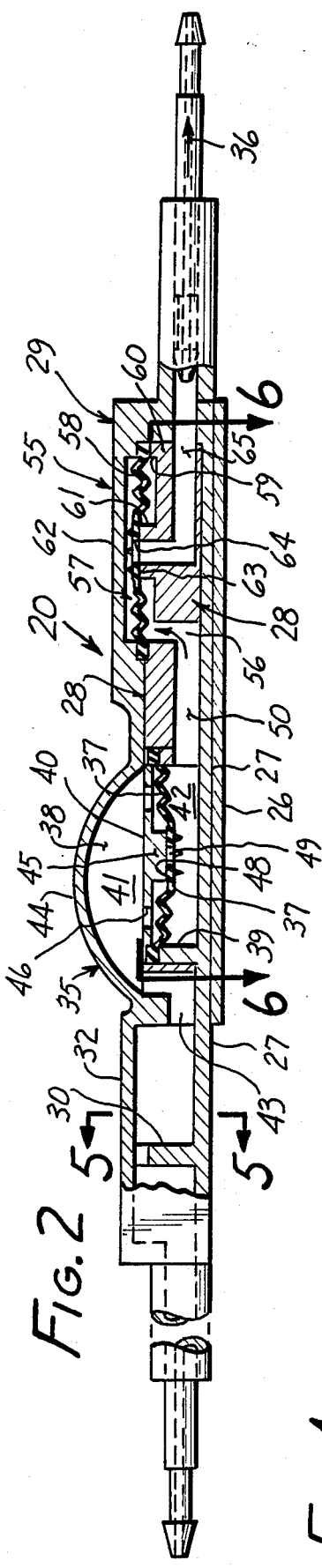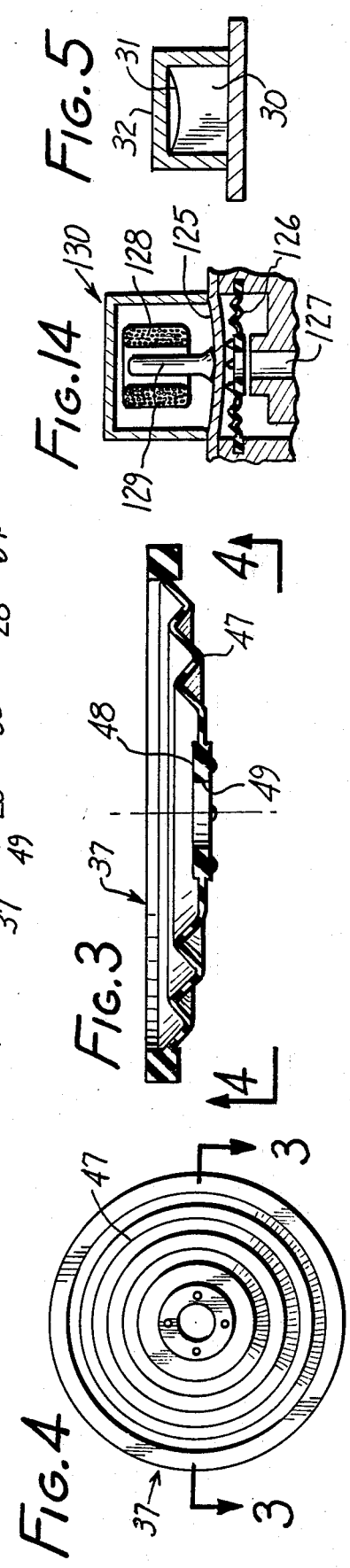

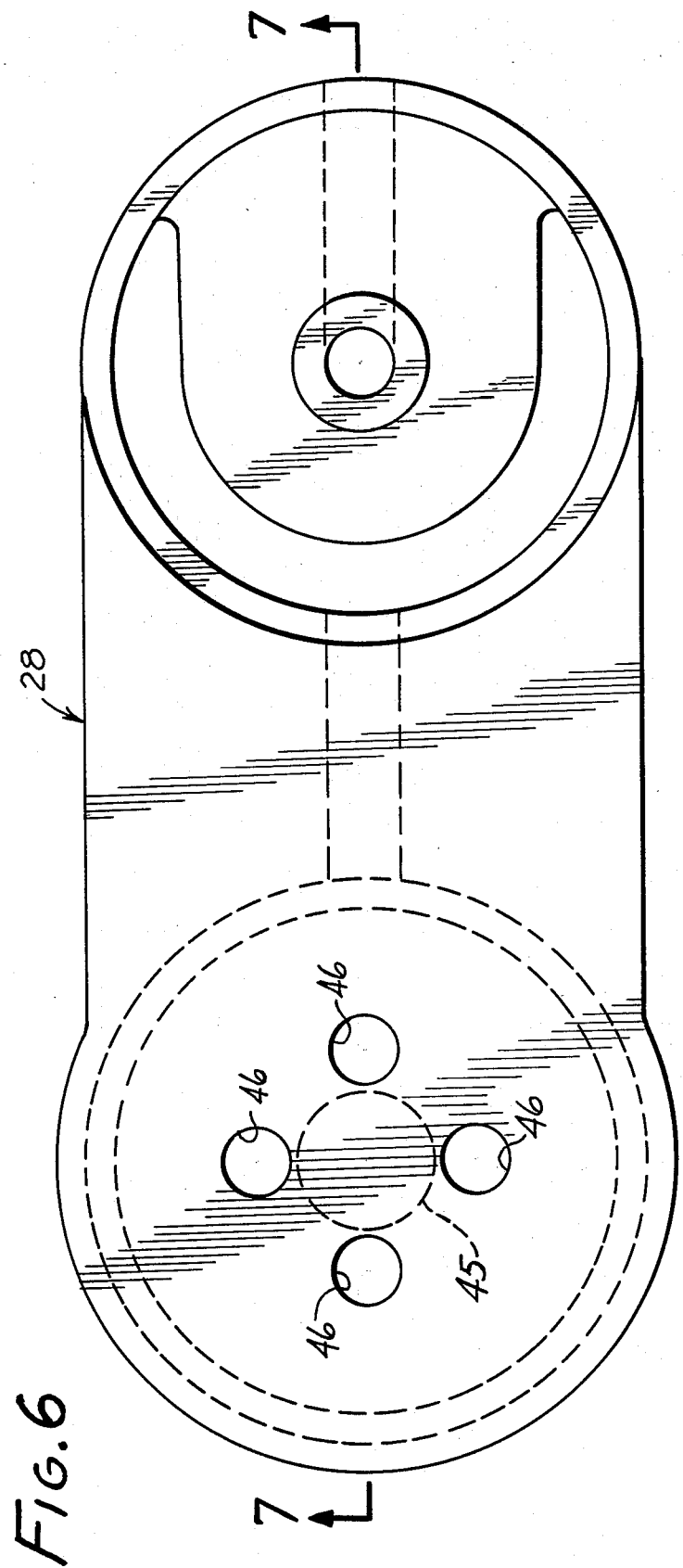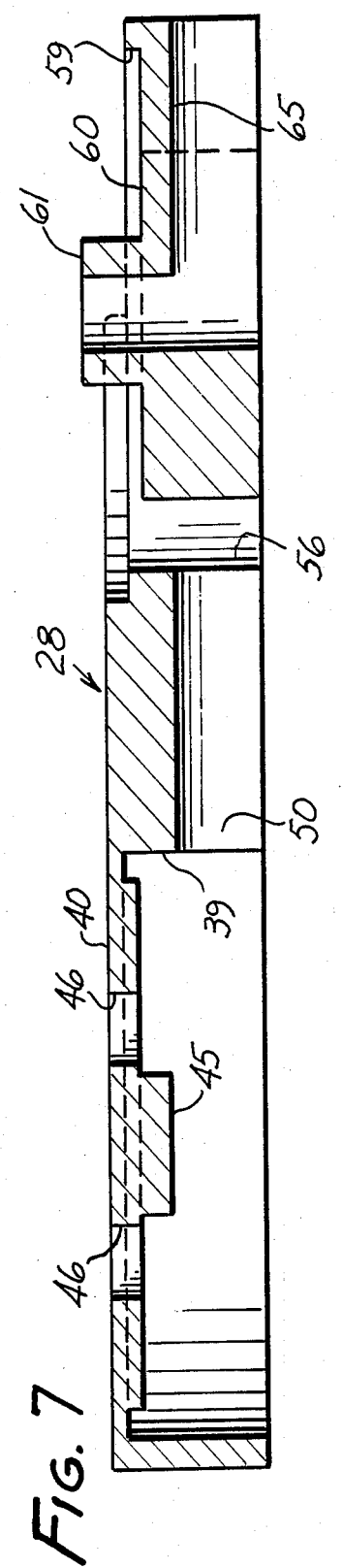

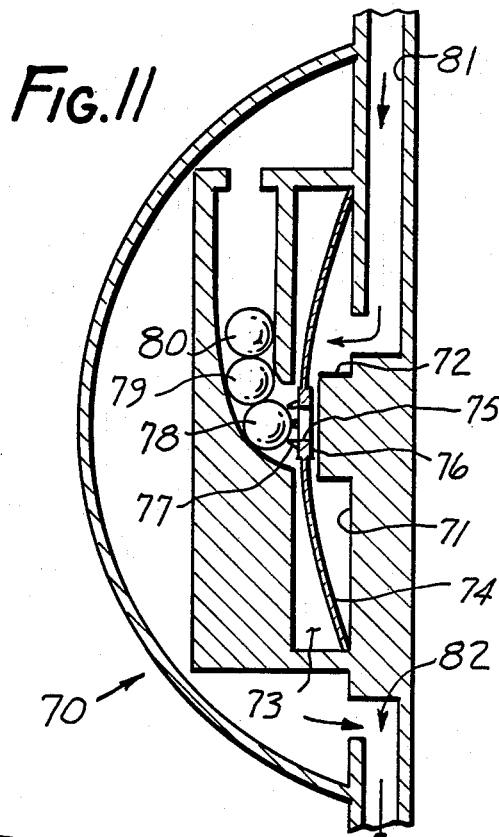
Fig. 11
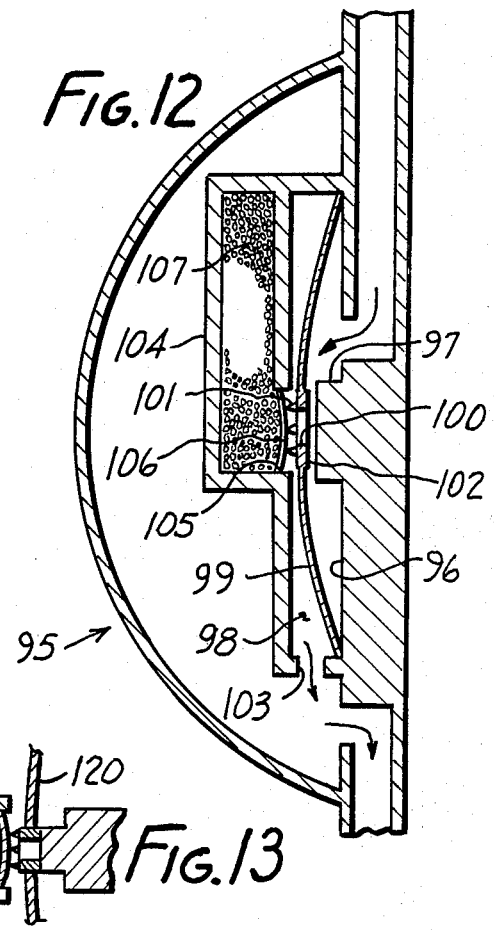
Fig. 12
Fig. 13
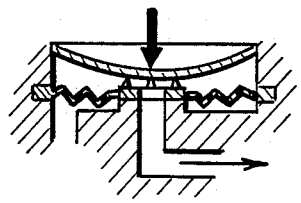
Fig. 8
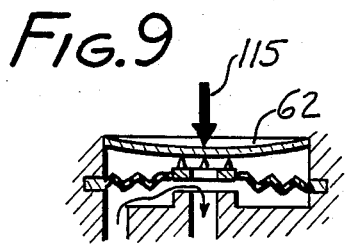
Fig. 9
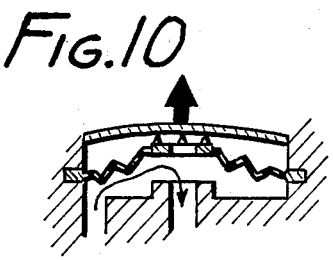
Fig. 10

4,867,741

PHYSIOLOGICAL DRAINING SYSTEM WITH DIFFERENTIAL PRESSURE AND COMPENSATING VALVES

FIELD OF THE INVENTION

This invention relates to drainage (shunt) systems to drain body fluid, for example, cerebrospinal fluid, from one body region to another body region.

BACKGROUND OF THE INVENTION

The drainage of cerebrospinal fluid to alleviate hydrocephalus is now an accepted and highly developed art. Early devices for this purpose were little more than a drainage tube with a unidirectional check valve which was often formed as a slit in the wall. These have now been superseded by systems which allow for a pumping action to withdraw fluid from a region, for flushing action to clear obstructions from the system, for routine flow at established differential pressures, and for minimizing excess drainage that can occur when the patient abruptly changes his position.

Excess drainage most frequently occurs when, after the patient has laid down for a time, he sits or stands up. Then the full system, which was nearly horizontal with only a small differential in elevation between the body regions, becomes nearly vertical with a tall column of fluid tending to flow out of the downstream end. This exerts a substantial suction in the system that can result in over-drainage.

As examples of the prior art, Schulte Pat. No. 3,111,125 shows a pumping device that is palpable from outside which enables the system to be flushed downstream of the pump, and for fluid to be pumped from upstream. Schulte Pat. No. 3,769,982 shows a system which has closure means responsive to downstream suction, in which an anti-siphon valve closes when downstream suction exceeds some predetermined level. These are commercially accepted systems, but they still suffer from some disadvantages which it is the purpose of this invention to overcome.

A variability of control, especially to prevent excessive drainage, is a desirable objective in systems of this type. It should be remembered that cerebrospinal fluid is being withdrawn from within and around the brain, and that either excessive pressure in, or excessive drainage of fluid from the cranium, are consequences to be avoided. Insufficient drainage results in the classical consequences of hydrocephalus—excessive pressure and possible brain damage. Excessive drainage results in acute discomfort with headaches, lassitude and mental obtundity or may chronically lead to the slit ventricle syndrome.

A valve which responds to an unfavorable circumstance such as suction with merely an off or on choice may be better than no control at all, but a compensating valve which can respond proportionally (even though closure may be one of the potential settings) is much to be preferred. A simplistic off/on choice is likely to confine the operation of the system to only certain circumstances, whereas it is much better if the drainage can be continuously controlled. This invention provides an improved differential pressure valve which not only responds to upstream and downstream pressure, but also to a third "reference" external force or pressure. It can be used for pumping and flushing, and as a compensating valve that can provide proportional settings between the three control pressures rather than merely off and on settings.

While cerebrospinal fluid drainage from the brain is disclosed herein as the best known use for this device, it is evident that the device is also useful to drain other fluid from other body regions. The invention is not to be limited to the disclosed use.

BRIEF DESCRIPTION OF THE INVENTION

A system according to this invention includes a tube adapted to extend from a first normally upper region of the body to a second normally lower region of the body. An example of a first region are the ventricles of the brain, and for a second region, an atrium of the heart. In this tube, there are included a differential pressure valve adapted for pumping and flushing action and a compensating valve. The system is adapted to regulate the flow of fluid in response to three parameters: upstream pressure, downstream pressure, and an external force or pressure.

The differential pressure valve has a cavity partly bounded by a deflectable dome, with a fixed valve seat and a deflectable diaphragm with a central flow port surrounded by a seal which normally closes against the seat.

The compensating valve has a body with a cavity in which there is located a valve seat that surrounds an outlet port. A diaphragm extends across the cavity and has a central valve seal surrounding a central aperture. This valve seal can bear against the seat and close the compensating valve to flow, or move away from it to enable flow at a rate determined by the spacing between the seal and the seat. This spacing is variable and is a function of upstream pressure, downstream pressure, and a mechanical force or pressure exerted on the diaphragm.

According to a preferred but optional feature of this invention, the mechanical force is exerted by a pressure-responsive wall over the cavity which responds to atmospheric pressure whereby potentially to press the valve seal toward the respective seat.

According to other optional features of the invention, the mechanical force may be exerted by means whose exerted force is proportional to the alignment of the valve relative to the vertical, or by a spring which converts the differential pressure valve from one responsive to a single differential pressure to one in which this function is variable.

The above and other features of this invention will be fully understood from the following detailed description and the accompanying drawings in which

BRIEF DESCRIPTION OF THE DRAWINGS

FIG. 1 is a plan view of the presently preferred embodiment of the invention;

FIG. 2 is an axial cross-section taken at line 2—2 in FIG. 1;

FIG. 3 is a cross-section of a diaphragm taken at line 3—3 in FIG. 4;

FIG. 4 is a bottom view taken at line 4—4 in FIG. 3;

FIG. 5 is a cross-section taken at line 5—5 in FIG. 2;

FIG. 6 is a plan view of a portion of the device of FIG. 1;

FIG. 7 is a cross-section taken at line 7—7 in FIG. 6;

FIGS. 8, 9 and 10 are fragmentary views showing various settings of the compensating valve; and FIGS. 11, 12, 13, and 14 are fragmentary cross-sections showing other embodiments of the compensating valve.

DETAILED DESCRIPTION OF THE INVENTION

The system 20 shown in FIG. 1 includes a flexible upstream tube 21 and a flexible downstream tube 22, both of which are connected to valve assembly 23 by respective connectors 24,25. The upstream tube is usually directly inserted into a ventricle of the brain or other first region to be drained, or is connected to a connection tube which itself leads to the brain. The downstream tube usually terminates in an atrium of the heart, or into the peritoneal cavity as a second region. The objective, of course, is to drain excess cerebrospinal fluid from the cranium and to transport it to some other region from which it will be disposed of by normal body processes. This is conventional shunt practice.

The valve assembly includes a plate-like sub-base 26 to which there is attached a base 27. In turn, this base is surmounted by an inner housing 28, atop which is a cover 29. These are joined together by adhesives to form the unitary structure shown in FIG. 2. After these parts are assembled together as shown there is formed between the base and the cover adjacent the left hand end in FIG. 2 an occlusion shoulder 30 with a curved upper edge 31 directly beneath the flexible portion 32 of the cover.

Sufficient pressure exerted through the skin and against the flexible portion will hold it against the curved upper edge and close the system to flow at this point. This part of the assembly is sometimes called an "occluder".

Downstream from the occluder there is a differential pressure valve 35 which permits flow in the downstream direction shown by arrow 36 when the pressure is sufficient to overcome the structural bias of a diaphragm 37. The base, the cover, and the inner housing form a cavity 38 with a peripheral sidewall 39. A partition 40 divides the cavity into an upstream chamber 41 and a downstream chamber 42. An inlet port 43 enters the upstream chamber. It will be noticed that the center of the dome-like portion 44 of the cap is somewhat offset from the central portion of the partition. This provides a convenient means for constructing the inlet port. The partition carries a valve seat 45 which is stud-like and is directed downwardly into the downstream chamber. The partition is pierced by four passages 46 which are symmetrically spaced around the valve. These passages communicate between the two chambers.

Diaphragm 37 extends across the downstream chamber, and is mounted to its peripheral wall. The diaphragm 37 in the preferred configuration is formed with a plurality of concentric waves 47. At its center, it has a valve seal 38 which is adapted to fit flat and tightly against valve seat 45 in its repose condition in the absence of sufficient differential pressure on the diaphragm to unseat it and open the valve. A flow passage 49 is formed centrally in the valve seal.

It will be seen that a differential pressure between the upstream and downstream chambers sufficient to overcome the inherent bias of the diaphragm will cause the valve seal to leave the valve seat and permit flow from the upstream chamber through the passages out through outlet port 50 to a compensation valve 55 which compensates for atmospheric pressure.

The compensation valve also is built up from the base. It includes an inlet port 56 which continues from outlet port 50 of the differential pressure valve. It rises into a vacity 57 across which a diaphragm 58 extends that makes a continuous peripheral joinder with the peripheral side wall 59 of the cavity. The base 60 of this cavity is formed on the inner housing. The inner housing supports a valve seal 61 which rises into the cavity and has a flat sealing surface. A pressure responsive wall 62 completes the enclosure of the cavity. This wall is deflectible and flexible in response to differential pressures exerted on its opposite sides.

Diaphragm 58 is similar to diaphragm 37. It includes a valve seal 63 with a flow port 64 through its center in fluid communication with outlet port 65. In the repose condition, when no differential pressure is exerted across the diaphragm, it is in its sealing position with the valve seal biased against the valve seat so as to close the same.

The entire construction may conveniently be made from medical grade silicon elastomer. Certain portions of it are required to be flexible, namely the dome-like portion 44 in the differential pressure valve and the pressure responsive wall 62 in the compensating valve. A convenient thickness at these portions is about 0.020 inches. The diameter of the diaphragms is approximately 0.352 inches and the diameter of the dome-like cap is approximately 0.50 inches. These dimensions indicate how small this effective system can be made.

FIGS. 11, 12 and 13 schematically illustrate another embodiment of the invention. Speaking broadly, a mechanical force is adapted to be exerted against the diaphragm in the compensating valve for control purposes yet to be described. In FIG. 1 the mechanical force is the consequence of a differential pressure across the pressure responsive wall. FIGS. 11, 12 and 13 show different techniques for exerting the mechanical force.

For example, in FIG. 11, a compensating valve 70 has a base 71, a seat 72 rising into a cavity 73, and diaphragm 74 extending across the cavity. The diaphragm has a flow port 75 through its center and a surrounding valve seal 76 adapted on seat to valve seat 72. A plurality of points 77 space the nearest of a plurality of balls 78, 79, 80 away from the flow ports so that fluid can flow therethrough. When the valve is in its upright position as shown, all of the balls as a stack exert a force against the diaphragm so as to press the valve seal towards the valve seat. Should the valve be laid on its side, then only the nearest ball 78 will exert its weight in that manner. Therefore, when the valve is in its upright position as shown in the drawing, there is a stronger mechanical force exerted than when the patient is lying down. The flow through the valve is from inlet port 81 through the cavity and the flow port, and out through the outlet port 82. The valve is shown in a flow-open position. The diaphragm will normally be biased closed in the repose condition.

In FIG. 12, a compensating valve 95 has a base 96, valve seat 97, cavity 98, and diaphragm 99. This diaphragm is identical to that shown in FIG. 11. It includes a central flow port 100, a plurality of points 101, and a central valve seal 102 surrounding the flow port. An outlet port 103 leads from the cavity. A chamber 104 closed at an opening 105 by a flexible membrane 106 contains a plurality of microspheres of substantial weight such as a sphere filled with a heavy metal or the chamber filled with liquid mercury. When the valve is in its upright position as shown, the weight of all of these bodies 107 is transmitted to the diaphragm to tend to close it. If the patient were lying down, only those immediately above the opening would transmit their force. Therefore, there is a greater mechanical force exerted against the diaphragm in the upright position than in the reclining position. And in both FIGS. 11 and 12 there is an intermediate condition in which an intermediate force is exerted.

FIG. 13 shows that the mechanical force can be exerted on a diaphragm 120 by a spring, whose compressive force can be adjusted by turning an adjustment screw 121.

FIG. 14 shows an electronically controlled variable pressure valve 130. A solenoid 128 and a movable core 129 cooperate to apply a force to a compensating diaphragm 125. The diaphragm 126 and valve seat 127 will be recognized as parts of valve 55.

The operation of the system will now be described. This system is implanted in accordance with conventional shunt techniques. The valve assembly will be placed in an area where the pressure is that of the atmosphere. Beneath the scalp is one such region. The skin transmits this pressure so that the dome of the differential pressure valve and the pressure responsive wall of the compensating valve both are substantially at atmospheric pressure, and atmospheric pressure is thereby useful as a reference in this preferred embodiment.

When cerebrospinal fluid fills the system, it is desirable for flow to be permitted at a rate and under certain circumstances which will keep a proper amount of fluid surrounding the brain, and neither overdrain it nor permit excessive pressure to develop. In the event that the region downstream from the occluder needs to be flushed, or for the system to be pumped, the finger is pressed against the flexible portion 32 (through the skin) so as to close the fluid passage at that point. Then pressing on dome-like portion 44 will cause pressure to increase in chamber 41 and propel fluid through passages 46. This will unseat valve seal 48 so that fluid flows through flow passage 49 and through outlet port 50, into the compensating valve where pressure can potentially unseat diaphragm 58. If it does, fluid will flow out of the outlet port 65 with considerable pressure and velocity so as to flush the downstream portion of the system. Release of the occluder and dome will permit the system to return to a stable condition.

In normal operation the fluid pressure builds upstream of the pressure differential valve. When pressure in chamber 41 sufficiently exceeds that of pressure in chamber 42 to overcome the bias of the diaphragm, the diaphragm unseats valve seal 48. Under normal circumstances, the pressure responsive wall in the compensating valve may assume a number of positions, but absent unusual differentials yet to be described, when the pressure in the inlet 56 rises sufficiently relative to pressure in outlet port 65 (which is transmitted to chamber 57 above the diaphragm), the diaphragm will lift the valve seal off of the seat and drainage flow can occur. This is a normal situation.

Another circumstance is shown in FIG. 9, where the atmospheric pressure shown by arrow 115 deflects the pressure responsive wall 62 toward the valve seat. Thus, the wall is "compensating" the flow orifice by reference to atmospheric pressure. If there is sufficient differential pressure to open the diaphragm, the diaphragm will tend to move the valve seat up toward and against the pressure responsive wall. It is best although not necessary for the diaphragm to be held off the pressure responsive wall by the tips on it in order that there can always be easy transmission of fluid to the region above the diaphragm. Now the position of the diaphragm is determined both by the differential pressure as exerted upwardly on the diaphragm and also by a mechanical force from another reference source such as the atmosphere exerted by the wall. Therefore, the opening between the valve seat and valve seal can vary substantially, depending upon the relationships between the upstream and downstream pressures and a mechanical force derived from atmospheric pressure. This enables the diaphragm to assume a number of positions instead of merely the singular on and off positions provided by the prior art. This can permit generally continuous drainage as necessary, rather than only intermittent drainage.

The safety feature of this invention is shown in FIG. 8, wherein there is a strong downstream suction such as would occur when the patient stands up. In this case, while the strong negative pressure would be transmitted to the upper side of the diaphram and therby contribute to a tendency to open the valve, this is resisted by strongly drawing down the pressure responsive wall with relationship to the mechanical force (from atmospheric pressure) which tightly closes the valve and resists over-drainage.

FIG. 10 shows a condition in which there is a sufficient differential pressure to open the valve to flow in which the atmospheric pressure is less than the chamber pressure there being no strong downstream suction. In this case it will be observed that the valve is open wider than it is in FIG. 9. In this event, the mechanical force is upward or negative in value rather than otherwise. This allows a desirable rapid run-off of fluid.

Thus, this system provides for convenient flow with the compensating valve adapted to resist extreme changes in suction and to vary the response of the valve in accordance with upstream pressure, downstream pressure and some kind of mechanical reference force. A force derived from atmospheric pressure is an example.

FIGS. 11, 12 and 13 show other embodiments wherein the mechanical force is differently derived.

In FIG. 11 when the valve is upright as shown, the entire weight of the train of balls is exerted against the diaphragm while if the patient lays down, the weight of only one is exerted against it. Thus, there is a greater mechanical force in the former than in the latter, so as to resist overdrainage.

In FIG. 12, the weight of all of the microspheres is exerted against the diaphragm when the patient is erect and the weight of only a portion of them when he is recumbent, with similar results.

In FIG. 13, the mechanical force is derived from the spring, and is independent of either atmospheric pressure or of position.

In FIG. 14, the mechanical force is derived from a physical force exerted by energizing the solenoid so as to shift the core (armature) toward the valve.

A particular advantage of diaphragms 37 and 58 in the FIG. 2 embodiment is that they act as double protection against reflux of downstream fluid. This is especially important in ventriculo-atrial shunts to prevent the reflux of blood. Then an open-ended catheter can be used, instead of the less-desirable slit-valve atrial catheter.

In every embodiment there is a reference mechanical force which is brought into play to calibrate and make variable the opening of the compensating valve.

This invention is not to be limited by the embodiments shown in the drawings and described in the description which are given by way of example and not of limitation but only in accordance with the scope of the appended claims.

I claim:

1. A compensating valve for inclusion into a system having a tube for the transport of cerebrospinal fluid from a first region in the body to a second region in the body, wherein the relative elevation of the two regions can change when the patient changes position, thereby creating the risk of possible overdrainage from the said first region, said compensating valve comprising:
    a body having an internal cavity, and including a base, a peripheral sidewall, and force means for exerting a mechanical force, said base and sidewall partially defining said cavity;
    a valve seat extending in said cavity having a circular seat facing away from said base, there being an outlet passage opening axially into said cavity inside said valve seat;
    a flexible diaphragm extending across said cavity making a fluid sealing fit with said peripheral wall, overlaying said valve seat, having a central seal so disposed and arranged in one axial position as to seal on said valve seat and having a central aperture within said seal, the body having an inlet port to said cavity on the same side of said diaphragm as said valve seat and said diaphragm facing said force means on the other side from the inlet passage, said seal being normally seated on said valve seat and being displaceable therefrom by a distance which is a function of inlet pressure, outlet pressure, and force applied to said diaphragm by said force means;
    a fluid-sealing barrier sealing the end of the body opposing the base to close the cavity at the side of the diaphragm away from the base;
    whereby when said inlet pressure sufficiently exceeds outlet pressure, the diaphragm tends to move said seal axially away from said valve seat in opposition to the tendency of the force means to move the seal toward the seat.

2. A valve according to claim 1 in which said force means is a flexible pressure responsive wall partially bounding the cavity and normally spaced from said diaphragm, said wall being normally subjected to atmospheric pressure and forming at least part of said barrier.

3. A valve according to claim 1 in which said force means is a weight means adapted to exert more weight in one alignment relative to the vertical than in another.

4. A valve according to claim 3 in which said weight means is a train of balls.

5. A valve according to claim 3 in which said weight means is a container of microspheres or liquid mercury metal.

6. A valve according to claim 1 in which said force means is a spring.

7. A valve according to claim 6 in which the force exerted by said spring is adjustable.

8. A valve according to claim 1 in which said force means comprises electrically responsive means.

9. A valve according to claim 8 in which said electrically responsive means comprises a solenoid-type assembly whose armature is adapted to exert said force.

10. A valving system for the transport of cerebrospinal fluid from a first part of the body to a second part of the body, wherein the relative elevations of the two parts can vary with changes in the position of the user, and consequent overdrainage is intended at least to be minimized, said valving system comprising:
    a differential pressure valve comprising a body having an internal cavity, a deformable dome bounding a portion of the cavity, a base bounding another portion of the cavity, a partition extending across said cavity and dividing the cavity into a first upstream chamber partially bounded by said dome, a second downstream chamber partially bounded by said base, an inlet port communicating with said first chamber and adapted to receive fluid to be drained, and an outlet port communicating with said second chamber, a deflectable pressure responsive diaphragm extending across said second chamber, said diaphragm having a flow port therethrough at a central area thereof, an aperture through said partition interconnecting said first chamber to that part of the second chamber which lies between said partition and said diaphragm, and a valve seat mounted to said partition so disposed and arranged as to close said flow port when the diaphragm is brought against it, and to leave the flow port open to flow when the diaphragm is displaced away from it, and
    a compensating valve according to claim 1 with its inlet port connected to the outlet port of said differential pressure valve, and its outlet port adapted to be connected to conduit means to drain fluid passed by said valve system.

11. A valving system according to claim 10 in which said force means is a flexible pressure responsive wall partially bounding the cavity and normally spaced from said diaphragem, said wall being normally subjected to atmospheric pressure and forming at least part of said barrier.

12. A valve according to claim 10 in which said force means is a weight means adapted to exert more weight in one alignment relative to the vertical than in another.

13. A valve according to claim 12 in which said weight means is a train of balls.

14. A valve according to claim 12 in which said weight means is a container of microspheres or liquid mercury metal.

15. A valve according to claim 10 in which said force means is a spring.

16. A valve according to claim 15 in which the force exerted by said spring is adjustable.

17. A valving system according to claim 10 in which occluder means is provided to prevent flow through the inlet port of the differential pressure valve.

* * * * *